(12) United States Patent
Boudaoud et al.

(10) Patent No.: US 7,836,756 B2
(45) Date of Patent: Nov. 23, 2010

(54) FUEL COMPOSITION SENSING SYSTEMS AND METHODS USING EMF WAVE PROPAGATION

(75) Inventors: Idir Boudaoud, Besancon (FR); Adrian Page, Antrim (GB); Alan McCall, Antrim (GB)

(73) Assignee: Schrader Electronics Ltd., Antrim, Northern Ireland (GB)

( * ) Notice: Subject to any disclaimer, the term of this patent is extended or adjusted under 35 U.S.C. 154(b) by 0 days.

(21) Appl. No.: 12/004,443

(22) Filed: Dec. 18, 2007

(65) Prior Publication Data

US 2008/0156065 A1 Jul. 3, 2008

Related U.S. Application Data

(60) Provisional application No. 60/875,439, filed on Dec. 18, 2006.

(51) Int. Cl.
*G01N 30/62* (2006.01)
(52) U.S. Cl. ..................................... 73/61.61
(58) Field of Classification Search .................. None
See application file for complete search history.

(56) References Cited

U.S. PATENT DOCUMENTS

| | | | | |
|---|---|---|---|---|
| 2,720,624 A * | 10/1955 | Gunst et al. | ................ | 324/668 |
| 2,772,393 A * | 11/1956 | Davis | ........................ | 324/204 |
| 3,256,482 A * | 6/1966 | Rosso | ........................ | 324/669 |
| 4,729,245 A | 3/1988 | Hansman, Jr. | ................ | 73/865 |
| 4,769,593 A * | 9/1988 | Reed et al. | ................... | 324/668 |
| 5,088,325 A | 2/1992 | Eichberger et al. | ......... | 73/304 C |
| 5,150,683 A * | 9/1992 | Depa et al. | ............. | 123/406.45 |
| 5,301,542 A | 4/1994 | Meitzler et al. | | |
| 5,414,368 A | 5/1995 | Ogawa et al. | ............... | 324/675 |
| 5,497,753 A | 3/1996 | Kopera | ........................ | 123/494 |
| 6,293,142 B1 | 9/2001 | Pchelnikov et al. | ........ | 73/290 R |
| 6,564,658 B2 | 5/2003 | Pchelnikov et al. | ........... | 73/866 |
| 7,276,916 B2 * | 10/2007 | Hammer | ..................... | 324/634 |
| 2004/0251919 A1 | 12/2004 | Stahlmann et al. | .......... | 324/663 |
| 2006/0103393 A1 | 5/2006 | Stahlmann et al. | .......... | 324/658 |
| 2006/0201234 A1 * | 9/2006 | Abe et al. | .................. | 73/53.01 |

OTHER PUBLICATIONS

Notification of Transmittal of The International Search Report and The Written Opinion of The International Searching Authority, or The Declaration from the Intrnational Searching Authority mailed on May 23, 2007.

(Continued)

*Primary Examiner*—Robert R Raevis
(74) *Attorney, Agent, or Firm*—J. A. Thurnau, Esq.; P. N. Dunlap, Esq.

(57) ABSTRACT

A flex fuel sensor is deployed in conjunction with the fuel transfer line (e.g. around a plastic fuel line) or at the bottom/side of a fuel tank. An RF signal of a constant frequency may be generated across a resonant circuit, which comprises of an inductor and a PCB trace capacitor, capacitor plates, semi cylindrical capacitor plates, or the like. Electromagnetic radiation is propagated into the passing fuel in the transfer pipe. The conductivity and dielectric properties of the fuel change the capacitance of the trace capacitor/capacitor plates. These changes are proportional to ethanol/alcohol content of the fuel and are preferably detected by a microcontroller, or the like, and then transmitted to a flex fuel vehicle Engine Management System.

25 Claims, 4 Drawing Sheets

OTHER PUBLICATIONS

Notification of Transmittal of The International Search Report and The Written Opinion of The International Searching Authority, or The Declaration from the Intrnational Searching Authority mailed on Dec. 4, 2006, International Application No. PCT/US2006/018039.
Notification of Transmittal of The International Search Report and The Written Opinion of The International Searching Authority, or The Declaration from the Intrnational Searching Authority mailed on Apr. 15, 2009, International Application No. PCT/IB2008/003071.
PCT International Preliminary Report on Patentability Issued Jun. 24, 2009 for PCT/US2007/025979.

* cited by examiner

FUEL COMPOSITION SENSING SYSTEMS AND METHODS USING EMF WAVE PROPAGATION

CROSS-REFERENCE TO RELATED APPLICATIONS

This application claims the benefit of U.S. Provisional Application No. 60/875,439, also entitled Fuel Composition Sensing Systems and Methods Using EMF Wave Propagation, filed Dec. 18, 2006, which is also incorporated herein by reference. This application is also related to U.S. patent application Ser. No. 11/431,912, filed May 10, 2006, entitled System and Method for Sensing Liquid Levels Using EMF Wave Propagation, and U.S. patent application Ser. No. 11/800,965, filed May 8, 2007, entitled Liquid Level and Composition Sensing Systems and Methods Using EMF Wave Propagation, both of which are additionally incorporated herein by reference.

BACKGROUND OF THE INVENTION

1. Field of the Invention

This invention relates generally to systems and methods for sensing types of liquids passing through a line or stored in fuel tanks and other containers. More particularly, the present invention relates to sensing the constituents of fuel in a Flexible Fuel Vehicle by propagating electromagnetic waves into a liquid container or fuel line. Particular embodiments of the present invention detect fuel composition and alcohol content in a fuel line of a Flex Fuel Vehicle.

2. Description of the Prior Art

Flex Fuel Vehicles (FFVs) are motor vehicles which are compatible with the use of alcohol as a significant constituent of the vehicle's fuel. Alcohol based fuels are an alternative type of renewable, transportation fuel made from bio-material, potentially reducing dependence on petroleum based fuels. A motorist may advantageously gain increased horsepower for better engine performance because alcohol based fuels typically have a higher octane rating than premium gasoline. Alcohol based fuels include "E85," a term for motor fuel blends of 85 percent ethanol and 15 percent gasoline. E85 is an alternative fuel as defined by the U.S. Department of Energy and is intended for use in FFVs. Ethanol and other alcohols burn cleaner than gasoline and is a renewable, domestic, environmentally friendly fuel. FFVs can typically be fueled on any blend of ethanol and gasoline, from 0% ethanol and 100% gasoline up to 85% ethanol and 15% gasoline (E85).

It is important for the Engine Management System (EMS) of an FFV to have information on the composition of the fuel, so that the EMS may adjust certain vehicle parameters to optimize vehicle performance, specifically fuel consumption, emissions control and engine power.

Motor vehicle operators generally rely on indirect methods of determining the amount of alcohol in an FFV's fuel tank. The most common method of establishing the alcohol content of the fuel remaining in a motor vehicle is to use software algorithms implemented in the Body Controller Module or EMS of the vehicle. Alcohol content of the fuel may be altered by the driver at each filling of the fuel tank as there is no requirement to continuously use E85 fuel or conventional gasoline. Algorithm-based systems are slow to react to changes in the fuel composition and are typically only accurate to plus or minus ten percent alcohol content. Furthermore, such systems are even more ineffective when employed in a motor vehicle with saddle fuel tanks or similar fuel storage arrangements where the fuel may not be uniformly mixed or where the fuel mixture might change over time as the vehicle is driven.

Direct measurement systems exist, but require installation of a mechanism inside, or in-line with, the fuel line. Repair, replacement, or adjustment of such an internal or in-line fuel composition measurement mechanism is problematic.

The prior art fails to provide a reliable, inexpensive, and accurate system and method of measuring the composition of fuel in a motor vehicle using a system that can be installed external to a fuel line, fuel tank, or the like.

SUMMARY

The present invention is directed to systems and methods which accurately measure the composition of fuel in a motor vehicle and more specifically the alcohol content of fuel in a motor vehicle, particularly ethanol, by means of a non-intrusive fuel composition sensor.

In particular, embodiments of the present invention may be used in FFVs to detect the percentage of ethanol content in the fuel. This information can be constantly reported to the EMS or Body Control Module of the FFV, allowing the EMS to respond accordingly, thereby promoting performance, efficiency and/or the like. Advantageously the present invention provides immediate accurate ethanol content information without any direct contact with fuel, minimizing emissions, risk of fuel leak, risk of major car breakdown failure, and/or the like.

In accordance with various embodiments of the present invention, a flex fuel sensor may be deployed in conjunction with the fuel transfer line (e.g. disposed around a plastic fuel line), at the bottom or side of a fuel tank, or otherwise disposed proximate to the fuel.

In accordance with a method of the present invention a resonant circuit is resonated at a resonant frequency, an inductor of the resonant circuit is positioned proximate to liquid in a space and a capacitor of the resonant circuit is positioned proximate to the liquid in the space. A change in an electrical parameter associated with the resonant circuit caused by a variation in at least one property of the liquid is measured.

Therefore, a flex fuel sensor of the present invention may comprise a resonant circuit, with a capacitor of the resonant circuit comprising plates disposed adjacent to a fuel space and an inductor disposed adjacent to the fuel space, whereby the fuel acts as a dielectric in the capacitor in a manner proportionate to the constituents of the fuel.

The space may be a liquid transmission line, a storage tank, or the like, as discussed above. In the case of a liquid transmission line, the capacitor of the resonant circuit might comprise a plurality of plates placed on either side of the liquid transmission line, or spaced apart semi-cylindrical conductive plates disposed about the liquid transmission line.

Positioning the inductor of the resonant circuit in close proximity to the space causes electromagnetic radiation to propagate into the liquid in the space, whereby the liquid acts as an electrical load to the resonant circuit in a manner proportionate to the constituents of the liquid.

In accordance with some embodiments of the present invention a signal of a constant frequency may be generated across a resonant circuit, which comprises an inductor and a PCB trace capacitor, capacitor plates, or the like. Electromagnetic radiation may be propagated into the fuel, such as the passing fuel in a fuel transfer pipe. The conductivity and dielectric properties of the fuel may impact upon the electromagnetic field and may change the capacitance of the capacitor, the trace capacitor, the capacitor plates or other such capacitive device or devices which comprise the resonant circuit. Such changes may be proportional to the constituents of the fuel and may, for example be representative of the alcohol/ethanol content in the fuel. Such changes may be detected by a microcontroller, or the like, and may be communicated to a second microcontroller, to the EMS, to a device external to the flex fuel sensor, and/or other device. Such communications may be asynchronous or may be synchronized to an external device, and may be triggered by a signal from an external device, and/or the like As such the present invention provides a non-invasive, cost effective solution, well suited, not only for original equipment applications but also for up-fit or retro-fit or the like. The present systems and methods are highly responsive and provide immediate information to, an EMS or similar device, allowing quick and accurate adjustments to be made which may facilitate improvement and/or maintenance of vehicle performance.

In accordance with embodiments of the present invention, a substantially sinusoidal RF signal of a constant frequency may be generated and coupled to a resonant LCR (inductance-capacitance-resistance) circuit. Alternatively or additionally, a parallel resonant circuit may be employed. An inductor, such as for example a coil of the resonant circuit, may be placed proximate a fuel line, fuel tank or the like, causing electromagnetic radiation to propagate into the fuel space. Alternatively or additionally, a capacitor of the resonant circuit may be placed around, adjacent to or otherwise disposed proximate to a fuel line, fuel tank or the like, causing electromagnetic radiation to propagate into the fuel space. Consequently, the liquid fuel inside the line or tank acts as an electrical load to the resonant circuit in a manner proportionate to the constituents of the fuel. The loading effect of the fuel may cause a shift in the resonant frequency of the circuit and/or a change in the Q (quality factor) of the resonant circuit. The loading effect of the fuel is determined by monitoring a change in one or more electrical parameters associated with the excited resonant circuit. For example, the voltage across the resistor in the resonant circuit can be monitored. Changes in this voltage are detected and analyzed by a system controller, the result of which is used to output a signal indicative of fuel composition. Alternatively or additionally, measurements may be taken from the capacitor/capacitors and/or the inductor/inductors comprising the resonant circuit as impacted by the loading effect of the fuel on the resonant circuit and/or the electromagnetic field. Such an impact may for example be detected by measuring an amplitude change in the frequency signal of the resonant circuit, a change in the resonant frequency of the resonant circuit and/or the like. Regardless, measurements may take the form of a digital and/or analogue, electrical, and/or magnetic signals.

The present systems and methods can sense and measure the composition of liquid in other transmission lines and/or containers and are not limited to the examples used in this description. The system can be used in a wide variety of scientific, consumer, industrial, and medical environments, as well as in vehicles as discussed herein.

The present systems and methods may employ auto-calibration hardware and software that enables a flex fuel sensor of the present invention to determine an optimum system operating frequency. In one embodiment of the present invention, the optimum system operating frequency is selected to be a frequency above or below the resonant frequency of the resonant LCR circuit. The choice of this operating frequency over the resonant frequency may allow for larger changes in voltage drop as impacted by changes in liquid composition. Preferably, the system of such embodiments is tuned to operate at a frequency between a lower and upper value.

In some embodiments of the present invention, auto-compensation is provided to help ensure that the measured electrical parameter provides an accurate indication of the liquid composition in the fuel line, fuel tank, fuel container, or the like, independent of variations in operating conditions, such as variations in ambient temperature, humidity, pressure and/or the like.

By measuring fuel composition in-line, the present systems and methods may provide an EMS or other engine control device dynamic, accurate fuel composition information regardless of the fuel storage system employed and ongoing mixing of fuel in saddle tanks or similar storage arrangements.

Embodiments of the present invention may include a physical or wireless data interface to facilitate external communication or transmission of raw data measurements, encoded measurements, compensated measurements, and/or the like from a flex fuel sensor to a central controller in the vehicle. Such information may be communicated: periodically; in response to a change; by request from the central controller; by request from an external device such as a diagnostic device; and/or in other manners.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings, which are incorporated in and form part of the specification in which like numerals designate like parts, illustrate embodiments of the present invention and together with the description, serve to explain the principles of the invention. In the drawings.

DETAILED DESCRIPTION

Figure 1:
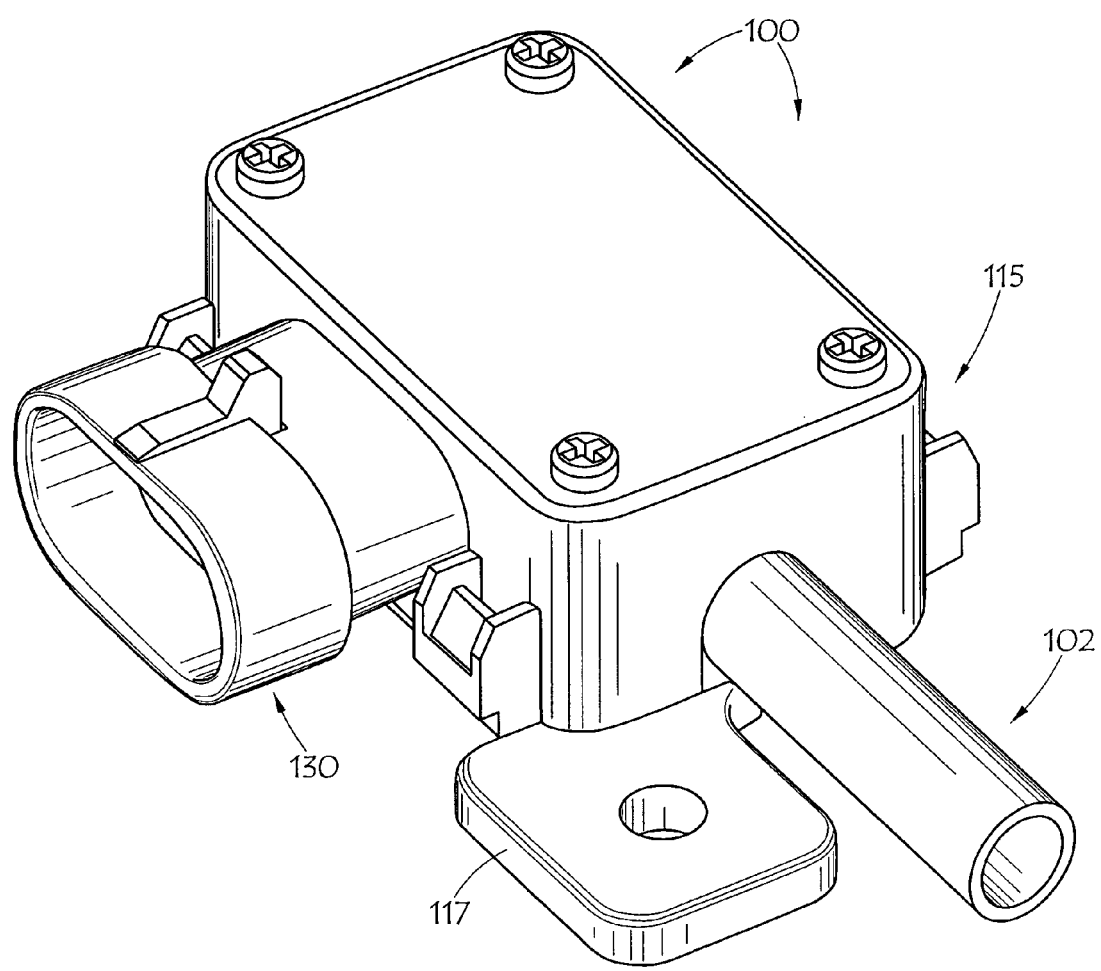
FIG. 1 is a perspective view of an embodiment of a flex fuel sensor of the present invention deployed in conjunction with a fuel line.
Figure 2:
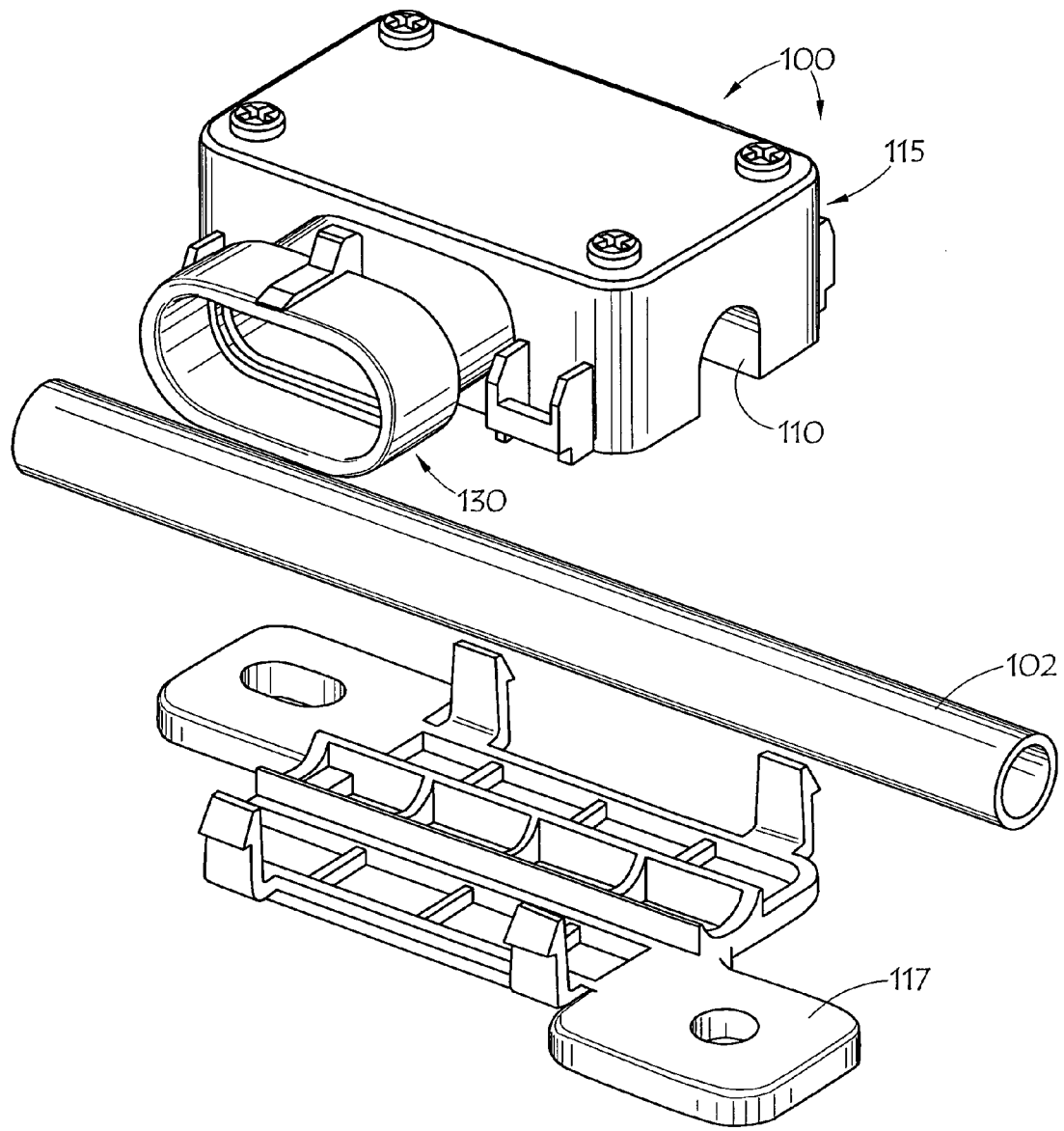
FIG. 2 is an exploded perspective view of the flex fuel sensor of FIG. 1.

FIGS. 1 and 2 show an embodiment of flex fuel sensor 100 of the present invention disposed in conjunction with fuel line 102, such as mounting flex fuel sensor housing 115 to base plate 117, encompassing fuel line 102. Alternative embodiments call for mounting a flex fuel sensor of the present invention to the side or bottom of a fuel tank. Generally, fuel line 102 or the aforementioned fuel tank is comprised of a non-conductive material such as plastic.

Figure 3:
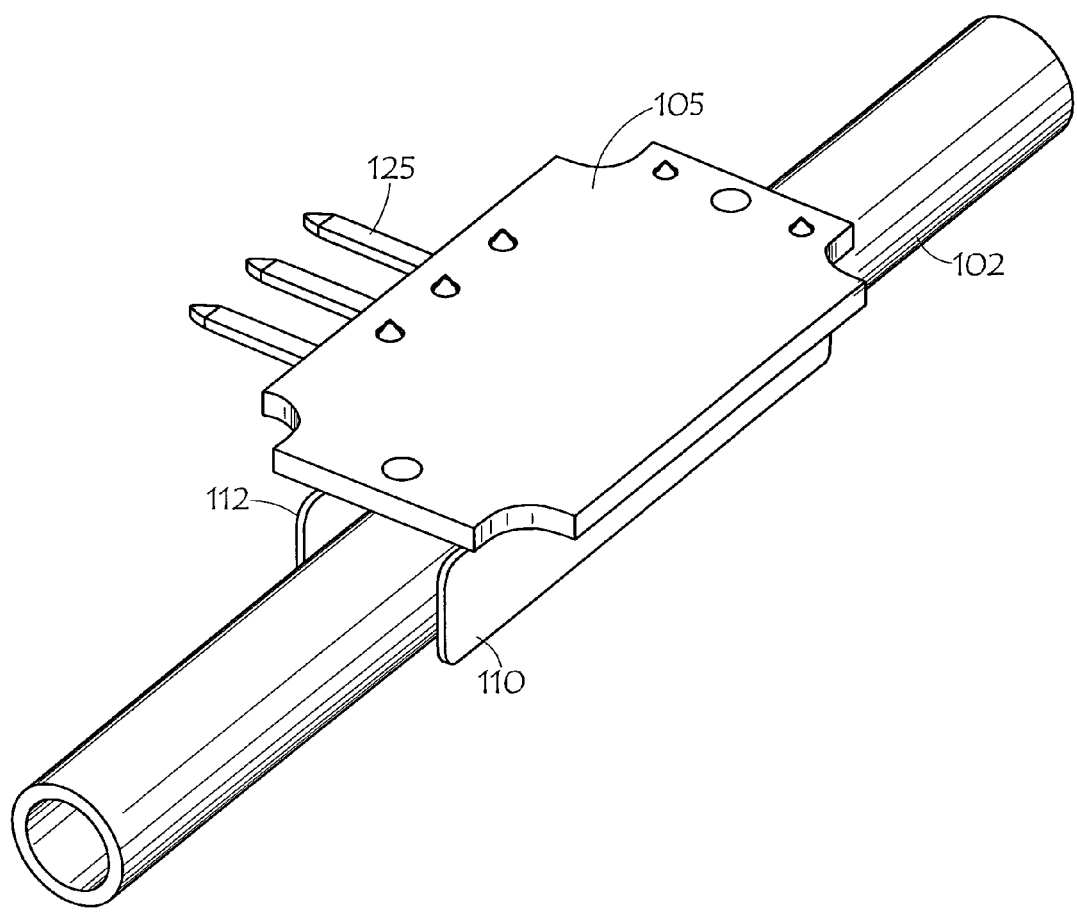
FIG. 3 is a rear side perspective view (relative to the perspective of FIGS. 1 and 2) of the PCB and capacitor plates of the flex fuel sensor of FIG. 1.

FIG. 3 illustrates an embodiment of PCB 105 and capacitor plates 110 and 112 of flex fuel sensor 100. Embodiments of flex fuel sensor 100 house PCB 105 in housing 115. PCB 105 may mount and/or define a controller, the controller including an RF generator and an analog-to-digital converter (ADC). PCB 105 might also include an antenna driver having output terminals, and input terminals, coupled to the RF generator and a resonant circuit coupled to the antenna driver and having an inductor positioned proximate a liquid in a container or fuel transmission line 102.

A flex fuel sensor of the present invention may comprise a resonant circuit, with a capacitor of the resonant circuit comprising plates disposed adjacent to a fuel space and an inductor disposed adjacent to the fuel space, whereby the fuel acts as a dielectric in the capacitor in a manner proportionate to the constituents of the fuel.

In the embodiment of FIGS. 1-3 a capacitor of an LCR circuit takes the form of a plurality of capacitor plates (110, 112). By placing an inductor of the resonant circuit in close proximity to a fuel line, electromagnetic radiation may be propagated into a fuel space defined within the line. Whereby, fuel in the line acts as an electrical load to the resonant circuit in a manner proportionate to the constituents of the fuel in the line. The conductivity and dielectric properties of the fuel change the capacitance of the trace capacitor/capacitor plates 110 and/or 112.

Figure 4:
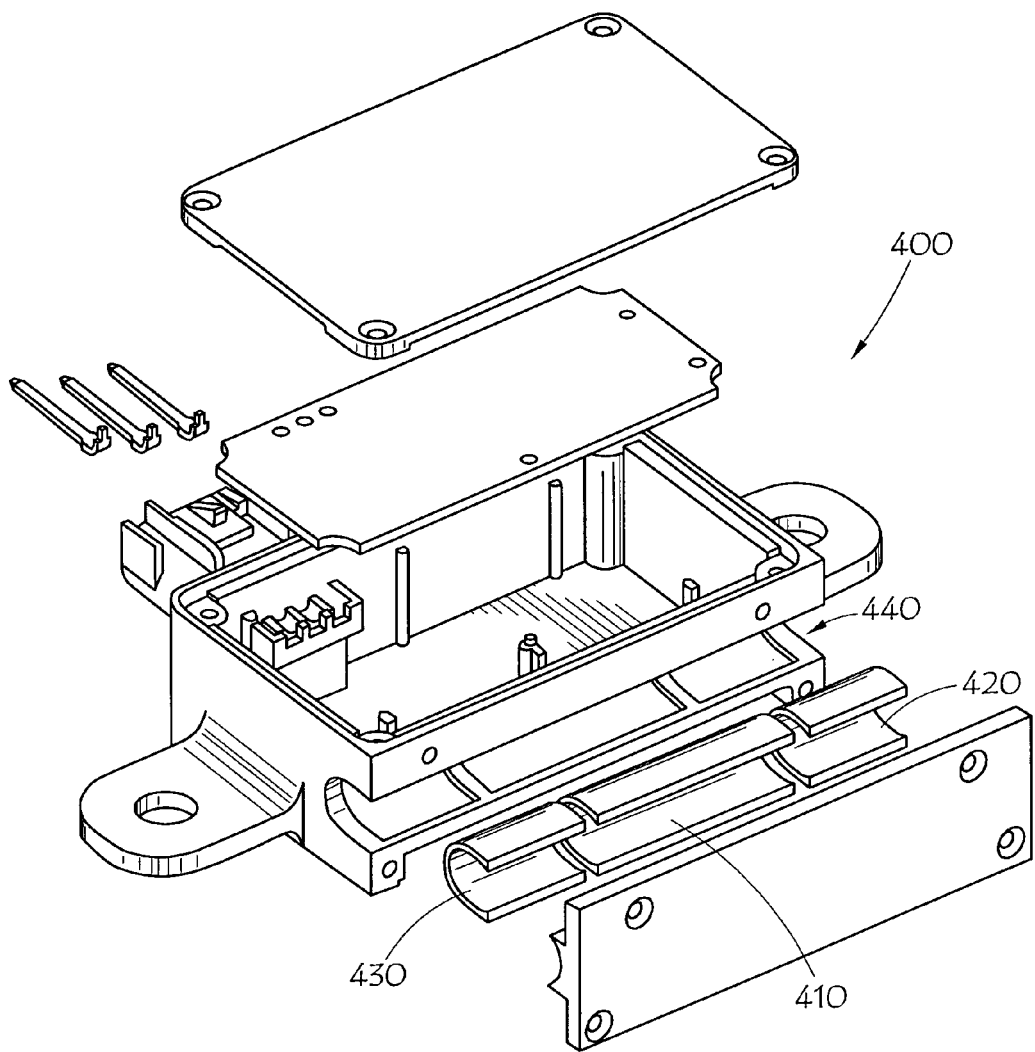
FIG. 4 is an exploded perspective view of another embodiment of a flex fuel sensor of the present invention, showing the PCB and semi-cylindrical capacitors.

In illustrated embodiment 400 of FIG. 4, a capacitor of an LCR circuit takes the form of a plurality of semi-cylindrical shaped capacitors 410, 420 and 430 of flex fuel sensor 100. This embodiment of the present invention may employ two semi-cylindrical capacitors giving a capacitive effect, or alternatively may have additional capacitors such as illustrated in order to increase the capacitance in the resonant circuit. Such semi-cylindrical shaped capacitors may fit into molded housing 440 and may be fixed around the fuel line using a sealing material such as for example a thermo plastic elastomer seal or other appropriate sealing material to adequately prevent contaminants and/or air between flex fuel sensor 100 and fuel line 102.

The present invention measures properties of a liquid, such as engine fuel. These properties are preferably electrical properties and a measured change in the electrical parameter of the liquid is a function of a variation in the electrical property of the liquid. Where the liquid is a fuel, the variation in electrical property may be a function of fuel composition. Measurements of electrical properties may include measuring a change in voltage at the resonant circuit and/or measuring a change in the resonant frequency of the resonant circuit.

Hence in accordance with a method of the present invention a resonant circuit is resonated at a resonant frequency, an inductor of the resonant circuit is positioned proximate to liquid in a space and a capacitor of the resonant circuit is positioned proximate to the liquid in the space. A change in an electrical parameter associated with the resonant circuit caused by a variation in at least one property of the liquid is measured.

In various embodiments of the present invention, the aforementioned RF generator generates an RF signal at an operating frequency of the resonant circuit and the antenna circuit is electrically coupled to the RF generator. The resonant circuit preferably has a frequency response curve centered around a resonant frequency. The controller may be operatively connected to the RF generator and to the antenna circuit and may be functional to cause the operating frequency of the RF generator to be proximate to the resonant frequency of the resonant circuit, and to measure a change in an electrical parameter associated with the resonant circuit as may be impacted by changes in for example the concentration of alcohol in the liquid passing through fuel line 102 or stored in the fuel tank or fuel container.

In an embodiment of the present invention changes in the properties of the fuel, such as for example changes in the dielectric properties of the fuel, the conductivity of the fuel, and/or the like, which may result from changes in the constituents of the fuel, may manifest as changes in the resonant frequency and/or properties of the resonant circuit. Such a change may be detected by sweeping between a first frequency and a second frequency to detect the new resonant frequency of the resonant circuit. Alternatively or additionally, changes in the properties of the fuel may manifest as changes to the amplitude of the resonant frequency signal of the resonant circuit.

The controller or similar circuitry of sensor 100 is preferably functional to monitor and/or communicate the measured change in the electrical parameter, such as via conductors 125 of sensor electrical connector 130. In particular, the controller may be further functional to convert the measured change in the electrical parameter to an alcohol concentration signal and to communicate the alcohol concentration signal to a flex fuel vehicle engine management system EMS, an external receiving device or the like.

Preferably, the present invention allows for calibrating the operating frequency of the RF signal to compensate for physical and/or electrical properties of the respective fuel line or container. This calibration may be carried out automatically. Such calibration might include adjusting the operating frequency of the RF signal so that an alcohol concentration sensing window is defined on a substantially linear part of a frequency response curve proximate the resonant frequency of the resonant circuit. The resonant circuit may be a series resonant circuit, and the controller may be a calibration module operative to cause the operating frequency of the RF generator to be on a substantially linear portion of the frequency response curve above the resonant frequency. Alternatively or additionally, calibrating the operating frequency might include sweeping the operating frequency of the RF signal in a range between a first frequency and a second frequency and measuring a parameter of the resonant circuit as the frequency of the RF signal is swept. In accordance with such embodiments, the controller might include a compensation module functional to adjust the alcohol concentration signal for changes in ambient temperature.

Thus, a change in voltage at the resonant circuit and/or a shift in the resonant frequency of the resonant circuit may be measured. The measurement may be carried out by sweeping between a first frequency and a second frequency to identify a resonant frequency of the resonant circuit. Also, the resonant frequency of the resonate circuit may be compensated for physical and/or electrical properties of a respective fuel line or container defining the space. This calibration may take place automatically. For example, calibration may be carried out by sweeping between a pair of frequencies to identify a resonant frequency of the resonant circuit as impacted by the space alone. Then, the measurement may be made by sweeping between a different, or the same, pair of frequencies to identify a resonant frequency of the resonant circuit as changed by the liquid in the space.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method comprising:
   resonating a resonant circuit at a resonant frequency;
   positioning an inductor of said resonant circuit sufficiently proximate to liquid in a space so that electromagnetic energy may propagate into the liquid for said liquid to influence said resonant circuit;
   positioning a capacitor of said resonant circuit sufficiently proximate to said liquid in said space for said liquid to influence the dielectric of said capacitor; and
   measuring a change in an electrical parameter associated with said resonant circuit caused by a variation in at least one property of the liquid.

2. The method of claim 1, wherein said space is a liquid transmission line.

3. The method of claim 1, wherein said space is a storage tank.

4. The method of claim 1, wherein said space is a liquid transmission line and said capacitor of said resonant circuit comprises a plurality of plates placed on either side of said liquid transmission line.

5. The method of claim 1, wherein said space is a liquid transmission line and said capacitor of said resonant circuit comprises spaced apart semi-cylindrical conductive plates disposed about said liquid transmission line.

6. The method of claim 1, wherein positioning said inductor of said resonant circuit in close proximity to said space causes electromagnetic radiation to propagate into said liquid in said space, whereby said liquid influences said resonant circuit by acting as an electrical load to the resonant circuit in a manner proportionate to an amount of one constituent of the liquid with respect to another constituent of the liquid.

7. The method of claim 1, wherein the liquid is a fuel and the variation is a function of fuel composition.

8. The method of claim 1, wherein the liquid is gasoline and the variation in is a function of alcohol content in said gasoline.

9. The method of claim 1, wherein said measuring further comprises measuring a change in voltage at the resonant circuit.

10. The method of claim 1, wherein said measuring comprises measuring a shift in the resonant frequency of the resonant circuit.

11. The method of claim 1, further comprising calibrating the resonant frequency to compensate for physical or electrical properties of a respective fuel line or container defining said space.

12. The method of claim 11, wherein the resonant frequency is calibrated automatically.

13. The method of claim 1, wherein said measuring comprises sweeping between a first frequency and a second frequency to identify a resonant frequency of said resonant circuit.

14. The method of claim 1, further comprising calibrating by sweeping between a pair of frequencies to identify a resonant frequency of said resonant circuit as impacted by said space, and wherein said measuring comprises sweeping between a different or the same pair of frequencies to identify a resonant frequency of said resonant circuit as changed by said liquid in said space.

15. A flex fuel sensor comprising a resonant circuit, a capacitor of said resonant circuit comprising plates disposed sufficiently adjacent to a fuel space such that said fuel acts as a dielectric in said capacitor in a manner proportionate to an amount of one constituent of the fuel with respect to another constituent of the fuel and an inductor disposed sufficiently adjacent to said fuel space so that electromagnetic energy may propagate into the fuel for said fuel to influence said resonant circuit.

16. The flex fuel sensor of claim 15, wherein said plates comprise a pair of conductive plates, each disposed on either side of said fuel space.

17. The flex fuel sensor of claim 16, wherein said fuel space is a fuel transmission line.

18. The flex fuel sensor of claim 15, wherein said fuel space is a fuel transmission line and said plates comprise a plurality of semi-cylindrical conductive plates disposed about, and spaced apart along, said fuel transmission line.

19. The flex fuel sensor of claim 15, wherein said fuel is gasoline and the variation in electrical property is a function of alcohol content in said gasoline.

20. The flex fuel sensor of claim 15 wherein a change in voltage at the resonant circuit is measured to determine constituents of said fuel.

21. The flex fuel sensor of claim 15 wherein a shift in a resonant frequency of the resonant circuit is measured to determine constituents of said fuel.

22. The flex fuel sensor of claim 15 wherein a resonant frequency of said resonant circuit is calibrated to compensate for physical or electrical properties of a respective fuel line or container defining said space.

23. The flex fuel sensor of claim 22 wherein said resonant frequency is calibrated automatically.

24. The flex fuel sensor of claim 15, wherein a resonant frequency of said resonant circuit is identified by sweeping between a first frequency and a second frequency.

25. The flex fuel sensor of claim 15, wherein said sensor is calibrated by sweeping between a pair of frequencies to identify a resonant frequency of said resonant circuit as impacted by said space alone, and a change in said resonant frequency caused by said liquid in said space is measured by sweeping a same or different pair of frequencies.

* * * * *